United States Patent
Larkins

(10) Patent No.: US 8,394,423 B2
(45) Date of Patent: *Mar. 12, 2013

(54) COMPOSITIONS COMPRISING APOCYNIN, GINKGO AND GINGER AND USES THEREOF

(76) Inventor: Nicholas John Larkins, London (GB)

(*) Notice: Subject to any disclaimer, the term of this patent is extended or adjusted under 35 U.S.C. 154(b) by 567 days.

This patent is subject to a terminal disclaimer.

(21) Appl. No.: 12/293,138

(22) PCT Filed: Mar. 14, 2007

(86) PCT No.: PCT/GB2007/000898
§ 371 (c)(1),
(2), (4) Date: Mar. 19, 2009

(87) PCT Pub. No.: WO2007/104985
PCT Pub. Date: Sep. 20, 2007

(65) Prior Publication Data
US 2009/0220624 A1    Sep. 3, 2009

(30) Foreign Application Priority Data
Mar. 16, 2006  (GB) .................................. 0605376.3

(51) Int. Cl.
*A61K 36/25* (2006.01)
*A61K 36/00* (2006.01)

(52) U.S. Cl. .................. 424/725; 424/756; 424/752

(58) Field of Classification Search .................. 424/725, 424/756, 752
See application file for complete search history.

(56) References Cited

U.S. PATENT DOCUMENTS

| | | | | |
|---|---|---|---|---|
| 6,274,177 | B1* | 8/2001 | Wu et al. ....................... | 424/756 |
| 6,492,429 | B1* | 12/2002 | Graus et al. .................... | 514/688 |
| 6,592,896 | B2 | 7/2003 | Rosenbloom | |
| 6,596,313 | B2 | 7/2003 | Rosenbloom | |
| 6,890,567 | B2 | 5/2005 | Nakatsu et al. | |
| 7,067,158 | B2* | 6/2006 | Larkins ......................... | 424/725 |
| 2003/0228383 | A1 | 12/2003 | Doshi et al. | |
| 2004/0126441 | A1 | 7/2004 | Pushpangadan et al. | |
| 2004/0156960 | A1* | 8/2004 | Villota et al. .................. | 426/325 |
| 2006/0253100 | A1* | 11/2006 | Burright et al. ............... | 604/512 |

FOREIGN PATENT DOCUMENTS

| | | |
|---|---|---|
| CN | 1657079 | 8/2005 |
| GB | 2 368 012 | 4/2002 |
| WO | WO 00/51576 | 9/2000 |
| WO | WO 02/04003 | 1/2002 |
| WO | WO 02/32435 | 4/2002 |
| WO | WO 03/043627 | 5/2003 |
| WO | WO 03/090769 | 11/2003 |
| WO | WO 2006/106350 | 10/2006 |

OTHER PUBLICATIONS

CAS Abstract 2006:308906.
"Nutritional Guide-products for healthy horses", URL:http://www.naf-uk.com/downloads/brochure.pdf; pp. 1-3 and 23-26 (2006).
International Search Report for corresponding PCT Application No. PCT/GB2007/000898 mailed Jun. 22, 2007.
UK Search Report for Application No. GB 0605376.3 dated Jul. 14, 2006.

* cited by examiner

*Primary Examiner* — Patricia Leith
(74) *Attorney, Agent, or Firm* — Knobbe Martens Olson & Bear, LLP

(57) ABSTRACT

A composition comprising *ginkgo biloba* or extract or component thereof; apocynin; and a gingerol. The composition may be used to treat diseases such as CF and COPD.

15 Claims, No Drawings

COMPOSITIONS COMPRISING APOCYNIN, GINKGO AND GINGER AND USES THEREOF

RELATED APPLICATIONS

This application is the U.S. National Phase under 35 U.S.C. §371 of International Application No. PCT/GB2007/000898, filed Mar. 14, 2007, designating the U.S. and published in English on Sep. 20, 2007 as WO 2007/104985, which claims priority under 35 U.S.C. §119(a)-(d) to United Kingdom Patent Application No. GB0605376, filed Mar. 16, 2006. The content of these applications is incorporated herein by reference in their entireties.

The present invention relates to preparations and compositions for the treatment or relief of disease; for example, diseases where excessive mucous is a problem, diseases where abnormal quantities of mucous are (or may be) problematic, and/or inflammatory disease (such as inflammatory respiratory diseases, for example asthma and/or allergic airways disease).

Chronic obstructive pulmonary disease (COPD) is characterised by a range of pathological changes of the respiratory system, including airflow limitation, inflammation, ciliary dysfunction, and increased mucous production. COPD also has significant systemic consequences. Although improving lung function and disease systems have been the main focus of COPD management, these parameters alone do not reflect the full burden of the disease. The term COPD encompasses a mixture of disease processes, the composition of which varies between individuals: these may include chronic bronchitis, small airway disease (for example, chronic bronchiolitis, laryngitis, pharyngitis), emphysema, and large airway disease (for example tracheitis). As COPD progresses, disruption of gas exchange can result in chronic hypoxia and cor pulmonale.

Cystic fibrosis (CF) causes the exocrine glands (which produce sweat and mucus) to produce abnormal secretions—unusually thick, sticky mucus that clogs the lungs and leads to chronic respiratory problems. The mucus also obstructs the ducts in the pancreas, preventing digestive enzymes from reaching the intestines and helping to properly digest food. As a result, people with cystic fibrosis have trouble breathing and absorbing nutrients and as well as eliminating non-digested food.

Other diseases or conditions that are associated with increased mucous production include inflammatory bowel disease such as irritable bowel syndrome, bowel parasite infections, mucoid enteritis, Crohn's colitis, vaginitis, ulcerative colitis, and post-operative gastrointestinal surgery symptoms or complications.

Asthma is recognized as a chronic inflammatory disorder of the airways in which many cells and cellular elements play a role (for example, mast cells, eosinophils, T lymphocytes, neutrophils, and epithelial cells). In susceptible individuals, this inflammation causes recurrent episodes of wheezing, breathlessness, chest tightness, and cough, particularly at night and/or in the early morning. These episodes are usually associated with widespread but variable airflow obstruction that is often reversible either spontaneously or with treatment. The inflammation also causes an associated increase in the existing bronchial hyper responsiveness to a variety of stimuli. The airway inflammation may be variably associated with changes in airway hyper responsiveness, airflow limitation, respiratory symptoms, and disease chronicity. The airway inflammation may be acutely and chronically associated with the development of airflow limitation as the result of bronchoconstriction, airway oedema, mucus secretion, and, in some patients, airway wall remodelling.

Aspergillosis is the name given to a wide variety of diseases caused by the genus of fungi *Aspergillus*. The most common forms are allergic bronchopulmonary aspergillosis, pulmonary aspergilloma and invasive aspergillosis. Compromised immune systems often allow *Aspergillus* to colonize.

There is a need for medicaments which may be used to treat or ameliorate (or prevent in at risk groups) disease by reduction of excessive mucous production (e.g. bringing mucous production back to normal levels), for example, excessive pulmonary mucous production. For example, there is a need for medicaments which treat or ameliorate the symptoms of COPD and CF, for example by reducing mucous production—e.g. by reducing excessive mucous production such as excessive pulmonary mucous production (and, for example, the consequent production of phlegm (sputum), which results in bouts of productive coughing). There is a need for medicaments to treat respiratory disease, for example inflammatory respiratory diseases such as asthma and/or allergic airways disease, and other inflammatory diseases such as Aspergillosis (*Aspergillus*). There is a need for medicaments to treat disease by treating abnormal (e.g. treating by reduction of) mucous production (for example pulmonary mucous production, abnormal mucous production in the gut, mucous production caused by allergic and/or immune reaction). There are an increasing number of people who are not able to use conventional pharmaceuticals (for example, due to allergies, side-effects or for ethical reasons). Thus, there is an increasing need for medicaments which are made of components from natural ingredients such as plant extracts, rather than conventional pharmaceutical compounds.

According to the present invention there is provided a composition comprising: *ginkgo biloba*, or extract (e.g. standardized extract) or component thereof; apocynin; and a gingerol. The composition may comprise *ginkgo biloba* or extract or component thereof; apocynin; and a gingerol; wherein at least 3.9% by weight of the composition is gingerol; and at least 0.05% by weight of the composition is apocynin.

The applicant has found that compositions according to the invention may have a remarkable effect in treating abnormal (e.g. reducing excessive) mucous production, especially excessive pulmonary mucous production. The applicant has found that compositions according to the invention may have a remarkable effect in treatment of inflammatory disease.

The applicant has surprisingly found that the use of a gingerol (or gingerols) in combination with *ginkgo biloba* (or extract or component thereof) and apocynin provides a substantial clinical improvement; and especially a substantial reduction in excessive mucous production. It is apparent that there is a beneficial, e.g. synergistic, clinical outcome when a gingerol (or gingerols) is added to a preparation comprising *ginkgo biloba* (or standardised extract or component thereof), and apocynin.

Herein, the term "gingerol" includes compounds such as 4-gingerol, 6-gingerol, 7-gingerol, 8-gingerol, 9-gingerol, 10-gingerol, 12-gingerol, 14-gingerol, 16-gingerol, dihydrogingerol(s), methyl-gingerol, and/or pharmaceutically acceptable salts thereof. The term "gingerol" includes these (and other) compounds, for example 6-gingerol, 8-gingerol, present as part of an unresolved mixture of compounds in the form of an unpurified plant or root extract. The term "gingerol" includes these (and other) compounds, for example 6-gingerol, 8-gingerol, which are present or used in a purified or synthetic form (e.g. a gingerol compound such as those mentioned above which has been synthesized, or which has been extracted from a plant, root etc. and purified). Further, the term gingerol also includes heat or transformation (or other) products such as mixtures of phenolic compounds with carbon side chains consisting of 7 or more carbon atoms, gingerdiones, gingerdiols, shogaols, paradols and zingerone, either in the form of plant extracts, or in purified or synthetic form. If a gingerol is present in compositions according to the invention as a direct extract from a plant (that is, as part of an unresolved mixture of compounds in the form of an unpurified plant or root extract), it may be referred to as a gingerol or gingerols "in the natural form" or "natural gingerol". For example, gingerol present in compositions according to the invention in the form of Zingiber Officinale (and other members of the Zingiberaceae family such as Languas galangal or Alpinia galangal commonly known as Galangal), other gingerol(s) containing plants such as *Aframomum melegueta*, phytochemical constituents of, for example, the Zingiberaceae family, and/or standardised extract(s) thereof, may be referred to as "natural gingerol". Alternatively or additionally, the gingerol may be used in the composition or preparation in a purified or synthetic form, and this may be referred to as "isolated gingerol". For example, if gingerol is present in compositions according to the invention as purified 6-gingerol and/or 8-gingerol or synthetic 6-gingerol and/or 8-gingerol (or other gingerol phytochemical or phytochemicals) this may be referred to as isolated gingerol. The term gingerol includes mixtures of two or more gingerols, as set out above.

The gingerol (or gingerols) may be present in the natural form, for example as Zingiber officinale or an extract thereof. The gingerol (or gingerols) in the natural form may be an extract which is standardised based on a standard amount of gingerols; such nomenclature is well known in the art. Thus, gingerol in the natural form (natural gingerol(s)) may comprise Zingiber officinale standardised to a gingerol fraction of between 1% and 10%, for example Zingiber officinale standardised to contain 5% gingerol. The gingerol in the natural form (e.g. Zingiber officinale standardised to 5% gingerol) may include one or more of 6-gingerol, 8-gingerol, 10 gingerol, and shogaols). In the Examples below, the natural gingerol (when present) is in standardised form and comprises Zingiber officinale standardised to 5% gingerol.

The gingerol (or gingerols) may be present in the isolated form, for example as 6-gingerol and/or 8-gingerol (present or used in a purified or synthetic form).

The compositions according to the invention may include at least 3.9% by weight of the gingerol (or gingerols). For example at least 5% by weight of the total composition may be gingerol (or gingerols), for example at least 10% by weight of the total composition may be gingerol (or gingerols), for example at least 15%, 20%, 25% or 30% by weight of the total composition may be gingerol (or gingerols).

The compositions according to the invention include apocynin. Apocynin is the plant-phenol 4-hydroxy-3-methoxyacetophenone.

Apocynin interferes with the arachidonic acid cascade, increases glutathione synthesis, and is a neutrophil oxidative burst agonist. The compositions (and preparations) of the invention may include an "isolated apocynin", which is apocynin which has been synthesized, or which has been extracted from plants and purified. The apocynin may be in isolated form (e.g. apocynin). The apocynin may be in the form of a precursor, for example the dimer, a Glucoside (for example androsin), a glycone, or in the form of acetovanillone). Apocynin may also (alternatively or additionally) be present in preparations or compositions according to the invention as direct extracts from apocynin containing plants such as *Picrorrhiza kurroa*, *Apocynum cannabinum*, *Apocynum venatum*, or *Apocynum androsaemifolium*, for example an extract from *Picrorrhiza kurroa* (for example as part of an unresolved mixture of compounds in the form of an unpurified plant or root extract); these extracts from apocynin-containing plants will be referred to as apocynin "in the natural form" or "natural apocynin". For example, apocynin present in preparations according to the present invention in the form of *Picrorrhiza kurroa* (or extract thereof) may be referred to as "natural apocynin". Natural apocynin or apocynin in the natural form may include androsin, glycosides of apocynin, and/or other iridoid glucosides, for example.

The apocynin may be used in the preparation as "isolated apocynin" and also as "natural apocynin". The use of the active entity in the natural form in combination with the "isolated" active entity may lead to a further beneficial, e.g. synergistic, effect between the isolated form (e.g. purified or synthetic apocynin) and the natural form (the apocynin contained in, for example, *Picrorrhiza kurroa*).

The natural apocynin may be *Picrorrhiza kurroa* in standardised form, such as is well known. The natural apocynin may be *Picrorrhiza kurroa* standardised to a total amount (by weight) of apocynin and/or androsin of between 1% and 60%, for example *Picrorrhiza kurroa* standardised to contain 5% apocynin and/or androsin, 10% apocynin and/or androsin, 15% apocynin and/or androsin, 20% apocynin and/or androsin, 25% apocynin and/or androsin, 30% apocynin and/or androsin, 50% apocynin and/or androsin. In the examples below, the *Picrorrhiza kurroa* is *Picrorrhiza kurroa* standardised to a total amount (by weight) of apocynin of 10%. It will be understood that other forms of natural apocynin may be used instead of or in addition to *Picrorrhiza kurroa*; such other forms may also be standardised to a total amount (by weight) of apocynin and/or androsin of between 1% and 60%, e.g. 10%.

The natural apocynin may be *Picrorrhiza kurroa* in standardised form based on standardised iridoid glucoside fractions such as are well known. The *Picrorrhiza kurroa* in standardised form may comprise standardised iridoid glucoside fractions collectively known as "Kutkin min 4%". Standardised iridoid glucoside fractions between Kutkin min 2% and Kutkin min 8% are also preferred. Kutkin is obtained by crystallisation and comprises the glucosides picroside I and kutoside in a ratio of 1:2 and other minor glycosides (Sing and Rastogi, 1972, Ansan et al., 1988).

At least 0.05% by weight of the composition may be apocynin. If the composition comprises apocynin in the form of *Picrorrhiza kurroa*, at least 0.5% by weight of the composition may be *Picrorrhiza kurroa*. The composition may include apocynin in an amount which is at least 1% by weight of the total composition. For example, at least 5% by weight of the composition may be apocynin, for example, at least 10%, 15%, 20%, 25% or 30% by weight of the composition may be apocynin.

The composition includes *ginkgo biloba*; or extract or component thereof. The *ginkgo biloba* may be in concentrated standard form, such as is well known in the art. For example, the *ginkgo biloba* may be a concentrated extract which is equivalent to four times the concentration of *ginkgo biloba* in the natural form, such as *ginkgo biloba* tablets sold by MediHerb of Australia (500 mg tablets containing *ginkgo biloba* concentrated extract equivalent to 2.0 g dry leaf *ginkgo biloba* standardised to contain 22-26% *Ginkgo* flavone glycosides). The composition may include a component of *ginkgo biloba*, for example a Ginkgolide or bilobalide. The component of *ginkgo biloba* may be one or more of Ginkgolide A, Ginkgolide B, Ginkgolide C, Ginkgolide J or Ginkgolide M. The composition may include Ginkgo biloba;

or extract or component therof in an amount which is at least 1% by weight of the total composition. For example, at least 5% by weight of the composition may be *ginkgo biloba*; or extract or component therof, for example, at least 10%, 15%, 20%, 25% or 30% by weight of the composition may be *ginkgo biloba*; or extract or component therof.

The composition may comprise ginkolide B, apocynin and gingerol-6. The composition may comprise ginkolide A, apocynin and gingerol-6. The composition may comprise ginkolide B, apocynin and gingerol-8. The composition may comprise ginkolide A, apocynin and gingerol-8.

The composition (or preparation) may further comprise an agent which enhances lipid solubility and/or lipid miscibility of the preparation. This may give rise to better absorption—e.g. intestinal absorption—and hence better bioavailability, especially by the oral route. The agent which enhances lipid solubility and/or lipid miscibility of the preparation may be a source of pharmaceutically acceptable surfactants and/or fatty acids, and/or a "gastroprotective agent". The agent which enhances lipid solubility and/or lipid miscibility of the preparation may be for example phosphatidylcholine (lecithin). Lecithin is mostly a mixture of glycolipids, triglycerides, and phospholipids (e.g. phosphatidylcholine, phosphatidylethanolamine, and phosphatidylinositol). However, in biochemistry, lecithin is usually used as a synonym for pure phosphatidylcholine, a phospholipid which is the major component of a phosphatide fraction which may be isolated from either egg yolk or soy beans from which it is mechanically or chemically extracted using hexane. It will be appreciated that the agent which enhances lipid solubility and/or lipid miscibility of the preparation may be pure phosphatidylcholine, or a mixture or mixtures of glycolipids, triglycerides and/or phospholipids (e.g. phosphatidylcholine, phosphatidylethanolamine, and phosphatidylinositol).

The preparations (or compositions) may further comprise additional components such as pharmaceutically conventional carriers, diluents, flavourings, emulsifiers and stabilisers. They may comprise additional components (for example carriers or diluents) which are "conventional" in herbal remedies.

The preparation may comprise one or more taste masking agents, for example yoghurt, fruit juice, honey and syrup.

The compositions and preparations may be suitable for oral administration. The methods of formulation of the compositions for oral administration are well known in the art. For example, the composition for administration may be prepared using a pharmaceutically acceptable carrier in a form suitable for administration. Such a composition can be prepared as a tablet, a pill, a sugar-coated agent, a capsule, a liquid, a gel, a syrup, a slurry, a suspension, etc. The carrier may be a herbal binder such as Glycyrrhiza glabra or one or more pharmaceutically acceptable carriers such as liposomes, lactose, trehalose, sucrose, mannitol, xylitol, crystalline cellulose, chitosan, calcium carbonate, talc, titanium oxide, or silica (silicon oxide) or the like.

The composition may be obtained, for example, by combining the active ingredients with a solid excipient, pulverizing the mixture (if necessary) and inserting into a capsule, for example, a soft sealed capsule consisting of a gelatin capsule, gelatin and coating (e.g., glycerol or sorbitol) or a capsule composition suitable for vegetarians. In the soft capsule, the composition may be dissolved or suspended in an appropriate liquid, such as a fatty oil, liquid paraffin or liquid polyethylene glycol, with or without a stabilizer.

The formulation (composition or preparation) may also be in the form of a standardised liquid extract. Standardised liquid extracts may in some circumstances have advantages when compared to the solid dose forms (tablets and hard shell capsules). They may involve minimal processing during manufacture and may reflect the true spectrum of the original herb (or plant etc.), in a compact and convenient form. There is also the possibility of superior bioavailability as the preparation is already in the liquid form. The prescribed dose may then be easily diluted (water, fruit juice, adding ice etc.) so as to minimise the experience of any unpleasant taste thus increasing the likelihood of patient compliance.

It will be appreciated that the preparations are suitable for other means of administration, for example mucosal delivery routes (for example rectal, nasal, vaginal) and also topical administration. The methods of formulation of the compositions for use in these methods are well known in the art.

The compositions, preparations and methods according to the invention are useful as (or in the manufacture of) pharmaceutical preparations for the treatment of human patients, and/or as (or in the manufacture of) veterinary preparations for the treatment of non-human animals, because they demonstrate activity as discussed below. The compositions may be used as (or in the manufacture of) veterinary preparations for the treatment of non-human animals, for example dogs, pigs, equine species (for example horses), poultry and reared game birds such as pheasants.

According to the present invention there is also provided a method of treatment or amelioration of a disease (or prevention of disease in at-risk groups or patients) in a human or animal subject comprising the step(s) of administering to the subject a composition comprising *Ginkgo biloba*, or extract or component thereof; apocynin; and a gingerol (or gingerols). The present invention also provides the use of *ginkgo biloba*, or extract or component thereof; apocynin; and a gingerol (or gingerols) in the manufacture of a medicament (composition) for the treatment or amelioration of a disease (or prevention of disease in at-risk groups or patients).

The method of treatment or amelioration (or prevention) of disease (or use) may be by reduction of excessive mucous production, e.g. reduction of excessive pulmonary mucous production. The method of treatment or amelioration (or prevention) of disease (or use) may (alternatively or additionally) be by treatment of abnormal (e.g. reduction of excessive) mucous production in one or more elements of the common mucosal system (such as the gastro intestinal tract and the vagina). The method or use may be for the treatment (or amelioration or prevention) of chronic obstructive pulmonary disease, CF, inflammatory disease, inflammatory respiratory disease and/or recurrent airway obstruction. The method or use may be for the treatment (or amelioration or prevention) of one or more of COPD, CF, chronic bronchitis, small airway disease, chronic bronchiolitis, laryngitis, pharyngitis, emphysema, large airway disease and/or tracheitis, asthma and/or asthma syndrome, recurrent airway obstruction, inflammatory bowel disease such as irritable bowel syndrome, bowel parasite infection, mucoid enteritis, Crohn's colitis, vaginitis, ulcerative colitis, post-operative gastrointestinal surgery, and Aspergillosis. The medicament or composition may further comprise an agent which enhances lipid solubility and/or lipid miscibility of the medicament/composition [for example phosphatidylcholine (lecithin)]. The method or use may be for the treatment (or amelioration or prevention) of disease in a human subject. The method or use may be for the treatment (or amelioration or prevention) of disease in an animal subject.

The composition may be administered to a human at a concentration, per daily dose, of Gingko biloba (standardised to gingko flavone glycosides—24%) of 1 mg/kg body weight—25 mg/kg body weight, preferably 2 mg/kg body weight—5 mg/kg body weight.

The composition may be administered to a human at a concentration, per daily dose, of a gingerol or gingerols of 60 µg/kg body weight—25 mg/kg body weight, preferably 1 mg/kg body weight—5 mg/kg body weight.

The composition may be administered to a human at a concentration, per daily dose, of apocynin of 60 µg/kg body weight—20 mg/kg body weight.

The method may further comprise the step of administering a natural form of apocynin, as described above, for example *Picrorrhiza kurroa*, for example, together with isolated apocynin. If *Picrorrhiza kurroa* is included, the preparation is administered at a concentration, per daily dose, of *Picrorrhiza kurroa* of 1 mg/kg body weight—35 mg/kg body weight, based on Picrorrhiza kurroa standardised to contain 10% by weight apocynin and/or androsin. If natural apocynin is included, the preparation is administered at a concentration, per daily dose, of natural apocynin of 1 mg/kg body weight—35 mg/kg body weight, based on a natural apocynin plant extract standardised to contain 10% by weight apocynin and/or androsin.

The daily dose may be provided as a single capsule, tablet or other solid or liquid form known to those skilled in the art, or may be provided in divided doses (for example 1 to 3 doses) to make up the full daily dose. The doses of gingko biloba, apocynin, and a gingerol or gingerols, may be provided together in the capsule, tablet etc, or the three may be provided as separate capsules or tablets (e.g. a capsule containing a dose or partial dose of gingko biloba, a separate capsule containing a dose or partial dose of apocynin, and a capsule containing a dose or partial dose of a gingerol or gingerols) for sequential administration.

For a veterinary preparation for treatment of allergic airways disease in a horse the composition may be administered at a daily dose, of Gingko biloba (standardised to gingko flavone glycosides—24%) of 0.5 to 5 g, for example 2 g. The composition may be administered at a daily dose, of apocynin of 0.5 to 5 g, for Example 2 g. The composition may be administered to a horse at a daily dose of gingerol (e.g. Zingiber Officinale) between 0.5 and 3 g, for example 1.5 g. The composition may be administered to a horse at a daily dose of Picrorrhiza kurroa between 4 and 10 g, for example 6 g, based on *Picrorrhiza kurroa* standardised to contain 10% by weight apocynin and/or androsin.

According to the invention there is provided a unit dosage form comprising between 70 and 3500 mg (for example between 100 and 200 mg) apocynin; between 70 and 3500 mg (for example between 200 and 300 mg) *ginkgo biloba* or extract or component thereof; and between 70 and 3500 mg (for example between 100 and 200 mg) gingerol. In a further aspect of the invention there is provided a unit dosage form comprising between 17.5 mg and 1050 mg (for example between 250 and 400 mg) natural apocynin (based on a natural apocynin [such as *Picrorrhiza kurroa*] which is standardised to contain 10% by weight apocynin and/or androsin); between 8.75 mg and 525 mg (for example between 100 and 200 mg) isolated apocynin; between 70 and 3500 mg (for example between 200 and 300 mg) *ginkgo biloba* or extract or component thereof; and between 70 and 3500 mg (for example between 100 and 200 mg) gingerol. The unit dose may be provided as a single capsule, tablet or other solid or liquid form known to those skilled in the art.

The present invention also provides the use of a gingerol in the manufacture of a medicament for the treatment of disease (such as CF or COPD). The treatment may be by the reduction of excessive mucous production, for example excessive pulmonary mucous production. The treatment may be by the reduction of excessive allergenic mucous production, for example excessive allergenic pulmonary mucous production. The present invention also provides a method of treatment or amelioration of a disease (such as CF or COPD) comprising the step(s) of administering to the subject a composition comprising a gingerol or gingerols. The treatment may be by the reduction of excessive mucous production, for example excessive pulmonary mucous production.

According to the present invention in a further aspect there is provided a composition including (% by weight) 5-25% (for example 15 to 20%) apocynin, 10-50% (for example 30-40%) Picrorrhiza kurroa, 10-45% (for example 20 to 30%) *ginkgo biloba* and 10-30% (for example 15 to 25%) Zingiber officinale. The *ginkgo biloba* may be a standardised 24% *Ginkgo* flavone glycoside extract.

According to the present invention in a further aspect there is provided a composition including (% by weight) 5-25% (for example 15 to 20%) apocynin; 5 to 50% (for example 10 to 20%) component of *ginkgo biloba* (e.g. Ginkgolide A, B, C, J or M); and 10 to 30% (for example 15 to 25%) gingerol (e.g. 6-gingerol, 8-gingerol).

The composition may further comprise an agent which enhances lipid solubility and/or lipid miscibility (for example lecithin).

The Zingiber officinale may be a standardised 5% gingerols extract. The composition may include apocynin, *Picrorrhiza kurroa*, *ginkgo biloba* and Zinziber officianale in the ratios (% by weight), for example 18: 36: 26: 20.

The compositions (and preparations) of the invention may be used as a sole treatment. They may also be used alongside conventional medicines (e.g. anti-allergics such as steroids and antihistamines which have unwanted side effects); this may lead to a reduction in the dose of conventional medicine required and thus a reduction in likelihood/occurunce of the side effects. A reduction of side effects of a therapeutic agent (for example the side effects of anti-allergic agents) during treatment of human or animal patients being treated is known as "dose sparing". Thus, according to the invention in a further aspect there is provided a method of dose sparing a therapeutic agent comprising the step of administering to the patient a composition comprising *ginkgo biloba*, or extract or component thereof; apocynin; and a gingerol (or gingerols) The composition may be administered at the same time as the therapeutic agent (for example the anti-allergic agent) or at a different time, by the same administration route, or by a different administration route. The medicament or composition may further comprise an agent which enhances lipid solubility and/or lipid miscibility of the medicament/composition [for example phosphatidylcholine (lecithin)].

DETAILED DESCRIPTION OF THE INVENTION

Examples of the present invention will now be described. In the following *Picrorrhiza kurroa* is obtained from SAMI Labs Limited, of Bangalore, India; apocynin (acetovanillone) is obtained from Sigma-Tau (Aldritch); *ginkgo biloba* and Ginger obtained from MediHerb (see above) and/or Cambridge Commodities Limited. These, lecithin, androsin, gingerols etc., and the other reagents are also widely available elsewhere.

EXAMPLE 1

The following reagents were mixed:
apocynin 180 mg
Picrorrhiza kurroa 360 mg (The above mixture of isolated and natural apocynin might also be described as: *Picrorrhiza kurroa* 540 mg enriched to contain a minimum of 33.33% apocynin—to do so would then combine both the *Picrorrhiza* and apocynin)
*ginkgo biloba* (standardised to contain 24% *Ginkgo* flavone glycosides) 260 mg
Zingiber Officinale (standardised to contain a minimum of 5% gingerols) 200 mg
The mixture was divided and prepared in a form suitable for dosing, for example, in a capsule form for oral dose.

EXAMPLE 1A

The following reagents were mixed:
apocynin 162 mg
*Picrorrhiza kurroa* 324 mg
(The above mixture of isolated and natural apocynin might also be described as: *Picrorrhiza kurroa* 540 mg enriched to contain a minimum of 33.33% apocynin—to do so would then combine both the *Picrorrhiza* and apocynin)
*ginkgo biloba* (standardised to contain 24% *Ginkgo* flavone glycosides) 234 mg
Zingiber Officinale (standardised to contain a minimum of 5% gingerols) 180 mg
Lecithin 100 mg
The mixture was divided and prepared in a form suitable for dosing, for example, in a capsule form for oral dose.

EXAMPLE 1B

The following reagents were mixed:
Apocynin: 180 mg
Ginkgolide A: 60 mg
6-Gingerol: 10 mg
Sodium carbonate (filler): 650 mg
Lecithin: 100 mg
The mixture was divided and prepared in a form suitable for dosing, for example, in a capsule form for oral dose.

EXAMPLE 1C

The following reagents were mixed:
Apocynin: 180 mg
Ginkgolide B: 60 mg
6-Gingerol: 10 mg
Calcium carbonate (filler): 650 mg
Lecithin: 100 mg
The mixture was divided and prepared in a form suitable for dosing, for example, in a capsule form for oral dose.

EXAMPLES 1D, 1E, 1F, 1G

These examples correspond with Examples 1, 1A, 1B, 1C, with the same weight of androsin substituted for the apocynin in each formulation.

The dose for adults and mature children for the reduction of excessive mucous production is 1,000 mg (two 500 mg capsules) in the morning and 1,000 mg (two 500 mg capsules) in the evening.

Administration of the above mixtures to patients with clinical histories, allergic or non-allergic, of chronic pulmonary disorders and subsequent chronic cough-related problems and which include patients with diagnosed COPD and asthma has provided significant clinical improvements which included reduction in excessive pulmonary mucous production, and reduction in coughing (both productive and non-productive). This is illustrated by the Examples, Case Studies, and Clinical Trial, below.

Concurrent with this significant reduction in excessive bronchial mucous production and subsequent reduction in coughing is a marked improvement in the reduction of breathlessness which enabled the resumption of normal daily activities such as shopping, walks and housework. A marked improvement in exercise tolerance has been reported by these patients. An improved nocturnal sleeping pattern has also been reported with minimal, if any, sleep disruption due to the need to cough and/or 'clear the throat' as a result of the ongoing excessive pulmonary mucous production. Increasing breathlessness and disability produces psychosocial consequences such as loss of confidence, loss of self esteem, increased dependency, social isolation, anxiety and depression. Patients after administration of the above mixture consistently report improvement in the 'quality-of-life' including an improved ability to socially-interact with others ('I can now go to clubs and cafes without worry'; 'I can walk without worry for as long as I wish'; 'I think I might go to the gym now—thanks to these capsules').

When patients have taken apocynin/*Picrorrhiza kurroa* and *ginkgo biloba* in the absence of Zingiber Officinale (gingerols) there has been some clinically observed relief. A substantial clinical improvement has been observed and reported when the combination of a gingerol or gingerols with the apocynin and *ginkgo biloba* is used.

The remarkable increase in effect which results from the combination suggests that a synergistic clinical outcome may be obtained by the combinations.

There now follow specific case studies and a description of a clinical trial:

EXAMPLE CS1

A 23 y.o. (year old) female presented with a long term history of chronic asthma complicated by sinusitis and bronchiolitis. The patient reported consistent productive production of thick stringy mucous production requiring removal by constant productive coughing. After taking the orally administered mixture of Example 1 the patient reported a much improved quality of life with much less excessive mucous production. The patient has a nearly normal respiratory system function with minimal, if any, excessive pulmonary mucous production. Whenever the patent stops taking this orally administered mixture the historical clinical symptoms reappear.

EXAMPLE CS2

A 70 y.o. male patient presented with a confirmed diagnosed chronic COPD and a long term history of taking daily inhaled corticosteroids and bronchodilators providing a minimal clinical benefit. After several days taking the orally administered mixture of Example 1 the patient reported some improvement (within 72 hours he reported no further coughing and no further excessive pulmonary mucous production). At the end of 30 days the patient reported that at long last he felt that he was now much better with far less coughing (as a result of less excessive pulmonary mucous production). Subsequently the patient now reports a much much improved quality of life with his COPD symptoms abated.

EXAMPLE CS3

A 16 y.o. female presented with diagnosed bronchiolitis—excessive pulmonary mucous production and constant nocturnal coughing. When the patient took Zingiber officinale standardised to contain a minimum of 5% gingerols (alone) some reduction of the mucous production and coughing was observed. However the clinical problem was not resolved and the clinical improvement was thought to be marginal. When the orally administered mixture according to Example 1 was administered a marked and dramatic clinical improvement was noted.

EXAMPLE CS4

A 92 y.o female with long term COPD inadequately managed with inhaled beta agonists and corticosteroids with a history of coughing excessive sputum (excess mucous production). Example 1A was instituted into her therapeutic regime by her attending physician and a marked positive clinical improvement was observed within the first 7 days. The patient—by her own request—continues to include Example 1A into her daily COPD therapeutic regime .

EXAMPLE CS5

An 80 y.o. male with long term COPD inadequately managed with inhaled beta agonists and corticosteroids with a history of coughing and sputum production (excess mucous). Example 1A was instituted into his therapeutic regime by his attending physician and a marked positive clinical improvement was observed. The patient—by his own request—continues to include Example 1A into his daily COPD therapeutic regime.

EXAMPLE CS6

An 84 y.o. female with long term bronchiolitis (COPD) inadequately managed with inhaled beta agonists and corticosteroids and antibiotics with a history of nocturnal sputum coughing (excess mucous) and respiratory embarassment. Example 1A was instituted into her therapeutic regime. A marked positive clinical improvement was observed within the first 14 days. The patient—by her own request—continues to include Example 1A into her daily therapeutic regime.

EXAMPLE CS7

An 80 y.o. female with long term COPD inadequately managed with inhaled beta agonists and corticosteroids with a history of sputum production (excessive mucous). Example 1A was instituted into her therapeutic regime by her attending physician and a marked positive clinical improvement was observed within the first 7 days. The patient—by her own request—continues to include Example 1A into her daily COPD therapeutic regime.

EXAMPLE CS8

A 72 y.o. male with COPD syndrome stated that "Now that I've been taking the AKL III [Example 1A] for just over two weeks [. . . ] I thought you might be interested in my reactions. Within three days my chest began to feel "clearer" ie less tightness and little or no phlegm. My wife tells me I also sleep more quietly! Generally I feel better and although the chest is not quite normal (I am still a bit throaty but that may just be catarrh) I would say that there was a real improvement without doubt.".

EXAMPLE CS9

74 y.o. female with long term COPD inadequately managed with inhaled beta agonists and corticosteroids and antibiotics with a history of non-productive coughing (excessive mucous production). Example 1A was instituted into her therapeutic regime and a marked positive clinical improvement was observed within the first 7 days. The patient—by her own request—continues to include Example 1A into her daily COPD therapeutic regime. On the occasions when she lowers the recommended dosage she notes a return of the coughing.

EXAMPLE CS10

A 28 yo Female with persistent long-term bronchitis and bronchiolitis with excessive diurnal and nocturnal sputum production (excess mucous) stated(translated direct from Spanish): "AKLIII [Example 1A] continues to work well. I can now work without problems. It appears that my body reacts very positively with respect to my respiratory functioning. Could you please continue to send me more AKL III (Example 1A) so that I might continue this fantastic path that returns me to good health."

EXAMPLE CS11

A 74 y.o female with pulmonary Aspergillus (IgE of 950/l) inadequately clinically managed with cortisone at 8 mg per day which is elevated to 40 mg for 3 days, 32 mg for 5 days and down to 8 mg during severe outbreaks. After 7 days including Example 1A in this therapeutic regime the patient observed that her clinical symptoms (breathlessness and persistent coughing) had much improved.

EXAMPLE 2

Clinical Trial

The effectiveness of Example 1A was assessed using a randomised placebo controlled double-blinded cross-over trial (University of Aberdeen—UK).

The purpose of the study was to provide scientific evidence regarding the efficacy and safety of Example 1A, a herbal mixture, as a therapy for adult patients whose asthma remains uncontrolled on standard medication.

Methods: 32 asthmatics (7 male, median (range) age 40.5 (22-73) yrs., median (range) FEV1% predicted 87.5 (33-93) %, median (range) daily ICS dose 800 (0-4000) mcg beclomethasone) completed a 36 week randomised double blinded placebo controlled cross-over trial consisting of: four week baseline, twelve-week treatment with Example 1A or identical placebo, eight week washout and further twelve-week cross-over treatment period. The change occurring over treatment periods was observed for lung function, Asthma Control Questionnaire (ACQ), Asthma Quality of Life Questionnaire (AQLQ), Leicester Cough Questionnaire (LCQ) scores. The mean (95% Confidence Interval) individual patient changes between active and placebo periods was calculated.

Results: Trends to clinical improvements favouring active treatment were consistently seen in the patient-centred outcomes: ACQ mean difference (active–placebo)=−0.35 (−0.78 to 0.07, p=0.10, AQLQ difference 0.42 (−0.08 to 0.93, p=0.09), LCQ difference 0.49, (−0.12 to 1.16, p=0.15). A change in ACQ and AQLQ score of 0.5 signified clinically relevant changes in asthma control or health status. On the ACQ, 28% were unchanged, 22% better on placebo and 50% better on Example 1A. On the AQLQ 29% had no change, 29% were better on placebo and 42% better on Example 1A. No significant differences in lung function were found (FEV1: (active–placebo) mean (95% CI) difference=0.01

(−0.12 to 0.14) L, p=0.9. PEF: −3 (−22 to 28) L/min, p=0.9). Nine exacerbations occurred during placebo treatment and five whilst on Example 1A. No significant treatment associated adverse events were noted.

Conclusions: The treatment was well tolerated. It is now well established that asthma symptoms correlate poorly with the level of airway obstruction as determined by the FEV1 and PEF. Following treatment, subjective improvement in asthma symptoms may occur without improvement in the level of airway obstruction. Example 1A provided consistent trends to symptom and quality of life improvements. When these were taken together a statistical significance with a 99.9% certainty was shown.

EXAMPLE 3

Study in Horses

The purpose of this study was to assess the ability of a dietary antioxidant supplement to prevent or delay the onset, decrease the magnitude of response and/or speed the recovery of lung dysfunction, clinical signs of disease, airway inflammation, and pulmonary oxidative stress in horses with recurrent airway obstruction (RAO) on exposure to organic dust.

Materials and Methods

The test horses were studied in a crossover design such that each horse received a placebo and an active supplement (Appendix 1) for 52 days with a 2-week washout-period in between. The placebo and supplement were assigned to each horse in a randomized order. The investigators were blinded to the identity of the treatments (labeled LC1 and LC2—one of which was a placebo supplement and as such a negative control and the other was the putative active supplement). After 6 weeks of supplementation horses were exposed to organic dust by stabling with straw bedding and hay for up to 3 days.

The performance of the placebo and active supplement was judged on the basis of responses in lung function, clinical examination, airway inflammation and pulmonary oxidative stress following organic dust challenge compared to responses on the placebo diet. Lung dysfunction was assessed by measuring airway reactance and airway responsiveness to histamine by forced oscillation mechanics. Clinical signs were assessed by assigning scores for respiratory rate, nasal discharge, abdominal lift/expiratory effort, nasal flaring, lung sounds and cough. Airway inflammation was determined by cytological analyses of tracheal wash and bronchoalveolar lavage fluid (BALF) samples, and by measuring the concentration of hydrogen peroxide in exhaled breath condensate (EBC). Oxidative stress was assessed by measuring the concentrations of reduced ascorbic acid, dehydroascorbate (DHA, oxidised ascorbic acid), reduced glutathione and oxidised glutathione in tracheal wash and BALF (See FIG. 1).

Results

All horses exposed to the organic dust challenge developed lung dysfunction, airway inflammation and pulmonary oxidative stress. There were no statistically significant differences between the first and second challenges for 23 of the 32 variables examined at the end-challenge time point. For the remaining variables there was an increase in BALF neutrophil numbers, EBC hydrogen peroxide concentration, end of challenge total clinical score and tracheal epithelial lining fluid (ELF) ascorbic acid redox ratio (ARR, ratio of DHA to total ascorbic acid), but a decrease in BALF mast cell numbers, and BALF and tracheal ELF concentrations of reduced ascorbic acid and total ascorbic acid, between the ends of the first and second challenges, irrespective of the order of treatment allocation.

Results of statistical analyses demonstrated that BALF ascorbic acid concentrations were higher after challenge in horses when fed LC2 compared to LC1 (FIG. 2) and that BALF DHA and ARR were lower after challenge in horses fed LC2 compared to LC1. All other parameters were not statistically significantly different between horses when fed LC1 compared to LC2.

Discussion

On the basis of these results there is evidence that when supplemented with LC2 horses had significantly less pulmonary oxidative stress than when supplemented with LC1 after exposure to organic dust. This suggests that (1) the supplement, administered in the diet, has a pulmonary effect and (2) that the LC2 supplement decreases the production or increases the consumption of reactive oxygen species. Despite significantly decreasing the severity of pulmonary oxidative stress induced by organic dust exposure, the LC2 supplement did not fully prevent pulmonary oxidative stress following organic dust exposure, which may explain the absence of significant differences between the supplements on lung function, airway inflammation or clinical examination scores. A higher dose of supplement may therefore be required to impact on these parameters. Inflammatory airway disease is a very common condition in the equine population, particularly racehorses. The LC2 supplement may have a beneficial effect on horses with this condition by decreasing pulmonary oxidative stress without contravening doping regulations.

Composition of Supplements.

EXAMPLE LC2

Active Supplement

The following table shows a list of the ingredients:
*ginkgo biloba* (standardized extract: *Ginkgo* flavone glycosides—24%) @ 2 g/day
Acetovanillone @ 2 g/day
*Picrorrhiza kurroa* @ 6 g/day
Zingiber officinale (standardized extract: gingerols—5%) @ 1.5 g/day
Lysoforte (lecithin) @ 1.5 g/day
Molasses meal @2 g/day
Lucerne meal @ 6 g/day
Orange peel @ 3.5 g/day
Supplement Dose/day: 25 g/day
LC1 (placebo—negative control ("Comparative Example"))
  Soya meal
Supplement Dose/day: 25 g/day

The invention claimed is:

1. A composition comprising *ginkgo biloba* extract; apocynin; and a gingerol; wherein at least 3.9% by weight of the composition is gingerol; 10-45% by weight of the composition is *ginkgo biloba* extract standardized to 22-26% *Ginkgo* flavone; and 5-25% by weight of the composition is apocynin.

2. A composition according to claim 1 wherein the gingerol is present in the composition as Zingiber Officinale.

3. A composition according to claim 2 wherein the Zingiber Officinale is standardised to between 1 and 10% gingerol.

4. A composition according to claim 1 wherein said gingerol is present in the composition as isolated gingerol.

5. A composition according to claim 4 wherein the isolated gingerol is one or more compounds selected from the group consisting of 4-gingerol, 6-gingerol, 7-gingerol, 8-gingerol, 9-gingerol, 10-gingerol, 12-gingerol, 14-gingerol, 16-gingerol, dihydrogingerols, methyl-gingerol and pharmaceutically acceptable salts thereof.

6. A composition according to claim 1 wherein said apocynin is in isolated form.

7. A composition according to claim 1 wherein the apocynin is present in the composition as one or more of *Picrorrhiza kurroa, Apocynum cannabinum, Apocynum venatum*, or *Apocynum androsaemifolium*.

8. A composition according to claim 1 comprising 10-30% by weight of gingerol or gingerols.

9. A composition comprising *ginkgo biloba* extract; apocynin; and a gingerol; wherein at least 3.9% by weight of the composition is gingerol; 10-45% by weight of the composition is *ginkgo biloba* extract standardized to 22-24% *Ginkgo* flavone; and 5-25% by weight of the composition is apocynin.

10. A composition according to claim 9 wherein 10-45% by weight of the composition is *ginkgo biloba* extract standardized to 24% *Ginkgo* flavone.

11. The composition according claim 1, wherein the gingko biloba extract comprises one or more of ginkgolide A, ginkgolide B, ginkgolide C, ginkgolide J or ginkgolide M.

12. A pharmaceutical or veterinary composition comprising a composition according to claim 1; and a pharmaceutically conventional carrier.

13. A unit dosage form comprising the composition according to claim 1.

14. A unit dosage form according to claim 13 further comprising between 50 and 500 mg lecithin.

15. The unit dosage form of claim 13 comprising, between 100 and 200 mg apocynin; between 200 and 300 mg *ginkgo biloba* extract standardized to 22-26% *Ginkgo* flavone ; and between 100 and 200 mg gingerol.

* * * * *